US 9,135,706 B2

(12) United States Patent
Zagorchev et al.

(10) Patent No.: US 9,135,706 B2
(45) Date of Patent: Sep. 15, 2015

(54) FEATURES-BASED 2D-3D IMAGE REGISTRATION

(75) Inventors: Lyubomir G. Zagorchev, Lebanon, NH (US); Robert M. Manzke, Cambridge, MA (US); Raymond C. Chan, Brookline, MA (US)

(73) Assignee: Koninklijke Philips N.V., Eindhoven (NL)

( * ) Notice: Subject to any disclaimer, the term of this patent is extended or adjusted under 35 U.S.C. 154(b) by 984 days.

(21) Appl. No.: 12/747,542

(22) PCT Filed: Dec. 1, 2008

(86) PCT No.: PCT/IB2008/055035
§ 371 (c)(1),
(2), (4) Date: Jun. 11, 2010

(87) PCT Pub. No.: WO2009/081297
PCT Pub. Date: Jul. 2, 2009

(65) Prior Publication Data
US 2010/0266220 A1    Oct. 21, 2010

(51) Int. Cl.
G06K 9/00         (2006.01)
G06T 15/00        (2011.01)
G06T 7/00         (2006.01)

(52) U.S. Cl.
CPC ..... *G06T 7/0028* (2013.01); *G06T 2207/10072* (2013.01); *G06T 2207/10121* (2013.01); *G06T 2207/10124* (2013.01); *G06T 2207/30048* (2013.01); *G06T 2207/30101* (2013.01)

(58) Field of Classification Search
None
See application file for complete search history.

(56) References Cited

U.S. PATENT DOCUMENTS

| 7,010,080 | B2 | 3/2006 | Mitschke et al. |
| 8,401,276 | B1 * | 3/2013 | Choe et al. ................... 382/154 |
| 2005/0004454 | A1 * | 1/2005 | Mitschke et al. ............ 600/427 |
| 2005/0094898 | A1 * | 5/2005 | Xu et al. ....................... 382/294 |
| 2008/0009698 | A1 * | 1/2008 | Boese et al. .................. 600/407 |
| 2008/0137940 | A1 * | 6/2008 | Kakinami et al. ........... 382/154 |
| 2008/0144925 | A1 * | 6/2008 | Zhu et al. ..................... 382/154 |

(Continued)

FOREIGN PATENT DOCUMENTS

| JP | 64088694 | 4/1989 |
| JP | 64088792 | 4/1989 |
| JP | 2006212294 | 8/2006 |

OTHER PUBLICATIONS

"Notes on the Harris Detector" lecture note for CSE576, University of Washington, Spring 05.*

(Continued)

*Primary Examiner* — Randolph I Chu

(57) ABSTRACT

An image registration apparatus comprises: a features detector (34) configured to extract a two-dimensional set of features (36) from a two-dimensional image (30) and to extract a three-dimensional set of features (38) from a three-dimensional image (32); a projection processor (40) configured to project three-dimensional data into two-dimensional projection data; and a registration processor (46, 52) configured to (i) adjust parameters to register the two-dimensional set of features and the three-dimensional set of features projected by the projection processor using a projection geometry (42), and to (ii) use the adjusted parameters to register the two-dimensional image and the three-dimensional image projected by the projection processor using the projection geometry.

17 Claims, 2 Drawing Sheets

(56) References Cited

U.S. PATENT DOCUMENTS

Figure 1:
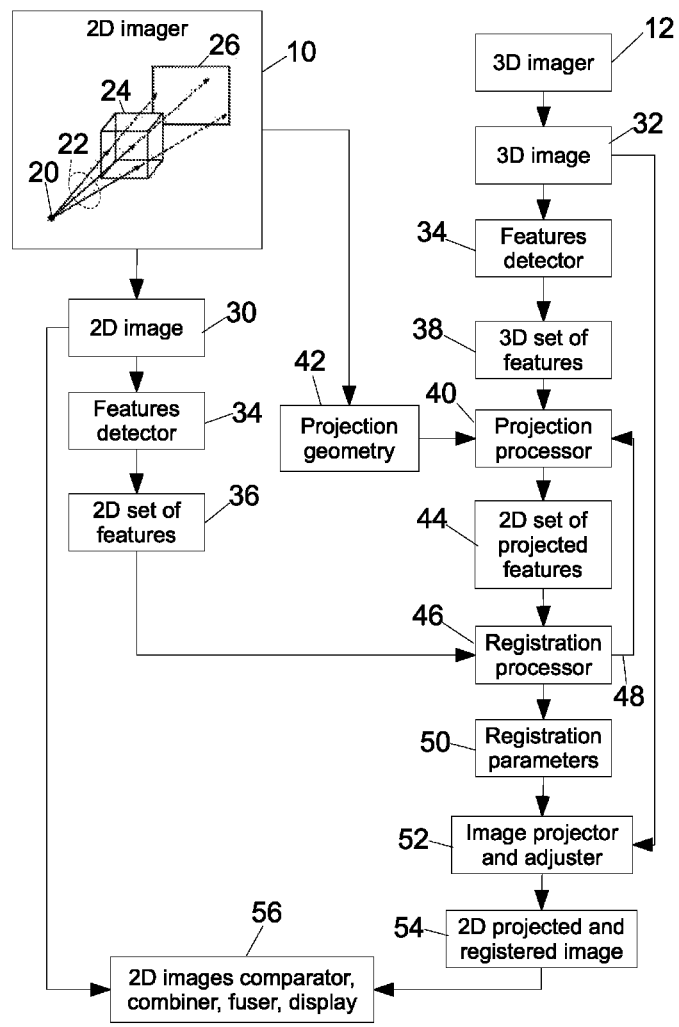

2010/0098327 A1* 4/2010 Se et al. .......... 382/154
2010/0189357 A1* 7/2010 Robin et al. .......... 382/195

OTHER PUBLICATIONS

Rohr et al.,"Point based Elastic Registration of Medical Image Data Using Approximating Thin Plate Splines",Visualization in Biomedical ComputingLecture Notes in Computer Science vol. 1131, 1996, pp. 297-306.*

Chen, X., et al.; Automatic 3D-2D Image Registration Using Partial Digitally Reconstructed Radiographs Along Projected Anatomic Contours; 2007; Medical Information Visualisation-Biomedical Visualisation; online; http://ieeexplore.ieee.org.

Kita, Y., et al.; A quick 3D-2D registration method for a wide-range of applications; 2000; IEEE Trans on Conf. on Pattern Recognition; vol. 1; pp. 981-986.

Livyatan, H., et al.; Gradient-Based 2-D/3-D Rigid Registration of Fluoroscopic X-Ray to CT; IEEE Trans on Medical Imaging; 22(11)1395-1406, Nov. 2003.

* cited by examiner

FEATURES-BASED 2D-3D IMAGE REGISTRATION

The following relates to the medical imaging arts. In some embodiments it relates to registering two-dimensional (2D) x-ray fluoroscopy images with three-dimensional (3D) images acquired by computed tomography, magnetic resonance imaging, or another imaging modality. More generally, however, the following relates to registering two-dimensional images acquired by any medical imaging modality with three-dimensional images acquired by the same or a different medical imaging modality.

In medical imaging procedures, it is sometimes the case that relevant imaging data is acquired using both two-dimensional and three-dimensional imaging. In some such cases, it is useful to generate and register a two-dimensional representation of the three-dimensional image with a corresponding two-dimensional image, so as to compare or combine information provided by the two techniques.

One example sometimes arises in interventional cardiac electrophysiology. During this procedure, x-ray fluoroscopy is sometimes used to visualize catheters or other interventional instruments. Advantageously, x-ray fluoroscopy images can be acquired using a "C-arm" type apparatus in which the x-ray tube and x-ray detector are mounted on opposite ends of the C-arm, and the patient is disposed in the gap. A C-arm type apparatus is relatively open, thus making the patient readily accessible to medical personnel. However, some soft tissue anatomy is not effectively imaged by x-ray fluoroscopy. Further, fluoroscopic images are typically acquired at a low x-ray dose, which can compromise resolution.

Accordingly, it is known to acquire pre-operative images of the patient before undergoing the cardiac electrophysiology procedure, using a three-dimensional imaging technique such as multi-slice computed tomography (CT) or magnetic resonance imaging (MRI), either of which provide better soft tissue contrast than x-ray fluoroscopy. The pre-operatively acquired CT or MRI images are then fused with the x-ray fluoroscopic images acquired during the cardiac electrophysiology procedure so that the CT or MRI images provide the missing soft tissue contrast.

CT or MRI images are typically generated for a three-dimensional volume; whereas, the x-ray fluoroscopy images are two-dimensional. It is known to mathematically project a three-dimensional image into a two-dimensional image using ray-casting techniques. Applying ray casting to the CT or MRI image produces a two-dimensional image. However, the mathematically projected CT or MRI image is generally not spatially registered with the x-ray fluoroscopic image, because the projection geometry of the x-ray fluoroscope respective to the patient generally differs from the projection geometry used in the mathematical generation of the CT or MRI projection. In some cases, further error may result due to distortions or other imperfections or artifacts in the x-ray fluoroscopic image and/or in the three-dimensional CT or MRI image.

The following provides improvements, which overcome the above-referenced problems and others.

An image registration process is disclosed, comprising: extracting a two-dimensional set of features from a two-dimensional image; extracting a three-dimensional set of features from a three-dimensional image; mathematically projecting the three-dimensional set of features into a two-dimensional set of projected features using a projection geometry; first registering the two-dimensional set of features and the two-dimensional set of projected features; and second registering the two-dimensional image and a mathematical projection of the three-dimensional image using parameters derived from the first registering.

A digital storage medium or media is capable of storing instructions executable by a digital system to perform the method of the preceding paragraph.

An image registration apparatus is disclosed, comprising: a features detector configured to extract a two-dimensional set of features from a two-dimensional image and to extract a three-dimensional set of features from a three-dimensional image; a projection processor configured to project three-dimensional data into two-dimensional projection data; and a registration processor configured to (i) adjust parameters to register the two-dimensional set of features and the three-dimensional set of features projected by the projection processor using a projection geometry, and to (ii) use the adjusted parameters to register the two-dimensional image and the three-dimensional image projected by the projection processor using the projection geometry.

Also disclosed is an apparatus comprising: a two-dimensional imager configured to acquire a two-dimensional image; a three-dimensional imager configured to acquire a three-dimensional image; a features detector configured to extract a two-dimensional set of features from the two-dimensional image and to extract a three-dimensional set of features from the three-dimensional image; a projection processor configured to project three-dimensional data into two-dimensional projection data; and a registration processor configured to register the two-dimensional image and the three-dimensional image projected by the projection processor using parameters adjusted to register the two-dimensional set of features and the three-dimensional set of features projected by the projection processor.

One advantage resides in faster 2D/3D image registration.

Another advantage resides in more accurate 2D/3D image registration.

Another advantage resides in faster interventional imaging.

Still further advantages of the present invention will be appreciated to those of ordinary skill in the art upon reading and understand the following detailed description.

The drawings are only for purposes of illustrating the preferred embodiments, and are not to be construed as limiting the invention.

FIG. 1 diagrammatically shows a 2D/3D multi-modality imaging apparatus.

Figure 2:
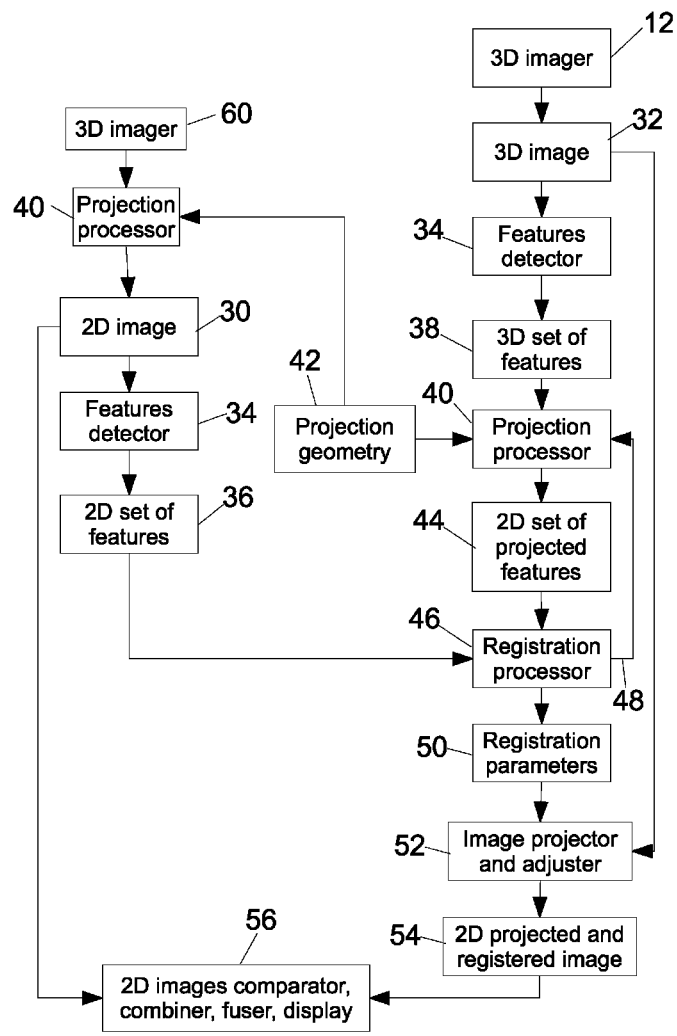

FIG. 2 diagrammatically shows a 3D/3D multi-modality imaging apparatus with registration of two-dimensional projections of three-dimensional images acquired by the different modalities.

With reference to FIG. 1, a 2D/3D multimodality imaging system includes a two-dimensional imager 10, such as an x-ray fluoroscopy apparatus, and a three-dimensional imager 12, such as a magnetic resonance imaging (MRI) system, a computed tomography (CT) imaging system, positron emission tomography (PET) scanner, a gamma camera, and so forth. The two-dimensional imager 10 is optionally capable of three-dimensional imaging but is used in the present 2D/3D imaging system as the two-dimensional imager. For example, the two-dimensional imager 10 is contemplated as a CT scanner operating without gantry rotation.

The two-dimensional imager 10 is a projection-type imager including a source 20, such as an x-ray tube in the case of an x-ray fluoroscopy apparatus, that transmits radiation 22 though an imaging region 24 containing a subject (not shown), such that a generally oppositely positioned two-dimensional detector array 26 detects the transmitted radiation as a function of position to form a two-dimensional image 30 of a projection-type. The two-dimensional image 30 therefore has a projection geometry characterized by projection parameters such as angulation, source position, detector position, or other geometrical parameters, and optionally also by projection parameters related to distortion, such as one or more distortion parameters characterizing the so-called "pincushion" distortion that is sometimes observed in x-ray fluoroscopes and other projection-type 2D imaging apparatuses. The projection geometry is at least approximately known, for example based on the nominal settings of the x-ray source and detector positions. In some embodiments, a precise calibration of the two-dimensional imager 10 provides highly precise projection parameters for the projection geometry, including precise geometrical parameters and quantitative values for the distortion parameters.

The three-dimensional imager 12 acquires a three-dimensional image 32. For example, if the three-dimensional imager 12 is an MRI, it acquires such a three-dimensional image 32 by sampling k-space three-dimensionally and reconstructing the k-space samples into the three-dimensional image 32. If the three-dimensional imager 12 is a CT scanner, it acquires projection data while the x-ray tube revolves around the subject, with the third dimension provided by having multiple rows of detectors (multi-slice CT) and/or by moving the patient in discrete increments or continuously (helical CT), followed by filtered backprojection or another reconstruction that reconstructs the projection data into the three dimensional image 32. Other approaches can be used, depending upon the type of three-dimensional imager 12 and the type of acquisition desired by the radiologist or other medical professional.

The relationship between the projection geometry of the two-dimensional image 30 and the spatial frame of reference of the three-dimensional image 32 is known approximately, based on how the subject is positioned in the two different imagers 10, 12. In some embodiments, this relationship is more precisely known, for example if the two different imagers 10, 12 are embodied integrally together as a hybrid imaging system, or a cross-imager mechanical alignment mechanism is used. In any case, however, there will generally be some misregistration between the two-dimensional image 30 acquired by the two-dimensional imager 10, on the one hand, and the three-dimensional image 32 acquired by the three-dimensional imager 12, on the other hand. This misregistration can take various forms or combinations of forms, such as rigid translational misregistration, rigid rotational misregistration, non-rigid translational and/or rotational misregistration, misregistration due to pincushion distortion or other types of distortion in one or both images 30, 32, and so forth. Accordingly, it is desired to mathematically project the three-dimensional image 32 to form a two-dimensional projection image, and to register this two-dimensional projection image with the two-dimensional image 30 acquired by the two-dimensional imager 10.

A features detector 34 processes the two-dimensional image 30 to extract a two-dimensional set of features 36 from the two-dimensional image 30. The features detector 34 also processes the three-dimensional image 32 to extract a three-dimensional set of features 38 from the three-dimensional image 32. In the embodiment of FIG. 1, the same features detector 34 is applied both to the two-dimensional image 30 and to the three-dimensional image 32; however, it is also contemplated to use two different features detectors, for example, wherein one of the feature detectors is optimized for two-dimensional images and the other feature detector is optimized for three-dimensional images. If two different features detectors are used in this fashion, the detected features should be comparable, such as of the same type.

The features detector 34 is capable of detecting, for example, corner features suitably represented as corner points. For detecting corner features, such a feature detector 34 operates via a corner detection algorithm such as for example by identifying high intensity gradient regions typically corresponding to corners by identifying locally maximum eigenvalues of an inertia matrix of the image gradient along each direction, and identifying a discrete set of line intersections. Advantageously, substantially the same corner features are generally detected for both the two-dimensional and three-dimensional images, even if the contrast mechanisms of the two imagers 10, 12 are substantially different (for example, x-ray versus magnetic resonance). The derivative-based nature of corner detection, coupled with a high likelihood of contrast for corner structures of the subject, ensures that the corner detection process is generally independent of contrast type, contrast level, and other image characteristics. Another advantage of using corner detection by the features detector 34 is that corner points are discrete in both two-dimensions and in three-dimensions.

The features detector 34 is alternatively or additionally also capable of detecting other types of features. For example, the features detector 34 is alternatively or additionally capable of detecting edge features. In some embodiments, the features detector 34 is capable of detecting edge features via an edge detection algorithm which is implemented as follows. Lines in the projected two-dimensional image correspond to the projection of interfaces within the three-dimensional image that are oriented along the x-ray beam 22. These interfaces are suitably detected by using the voxel intensity gradient magnitude and interface direction, along with the x-ray beam direction known from the projection geometry. The interface locations can be mapped from 3D to 2D using the projection matrix of Equation (2) to form a map of edge and corner locations.

In general, the features detector 34 reduces the respective images 30, 32 into two-dimensional or three-dimensional sets of features 36, 38 respectively, that are smaller respective subsets of data and therefore are readily correlated in space and are more efficiently processed from a computational standpoint as compared with the full images 30, 32. The respective sets of features 36, 38 retain the geometries of the source images 30, 32. Thus, for a features detector 34 that detects corner features, the two-dimensional set of features 36 comprises a set of points in a plane, while the three-dimensional set of features 38 comprises a three-dimensional "cloud" of points. Similarly, for an edge detector the two-dimensional set of features 36 comprises a set of lines lying coplanar in a plane, while the three-dimensional set of features 38 comprises a three-dimensional arrangement of lines.

A projection processor 40 mathematically projects the three-dimensional set of features 38 in accordance with a projection geometry 42 that is at least initially set to the projection geometry used by the two-dimensional imager 10 in acquiring the two-dimensional image 12. For an illustrative interventional C-arm x-ray fluoroscopy apparatus such as the Allura XPer FD10 (available from Philips Medical Systems, Eindhoven, the Netherlands), the projection geometry is suitably defined as follows. A vector, s extends from iso-center to the x-ray source 20, while a vector d extends from iso-center to a center of the detector 26. Two normals $n_1$ and $n_2$ define the detector plane, and are known for every projection. Any three-dimensional point P can therefore be mapped (i.e., projected)

to a two-dimensional point p on the detector 26 given any particular C-arm angulation. Expanding these vectors into Cartesian coordinates yields:

$$s = [s_x, s_y, s_z]^T$$

$$d = [d_x, d_y, d_z]^T$$

$$n_1 = [n_{1x}, n_{1y}, n_{1z}]^T$$

$$n_2 = [n_{2x}, n_{2y}, n_{2z}]^T$$

$$P = [X, Y, Z]^T$$

$$p = [u, v, \mu]^T \quad (1).$$

The matrix vector equation defining the projection geometry 42 can be written as:

$$\begin{bmatrix} u \\ v \\ \mu \end{bmatrix} = \begin{bmatrix} n_{1x} & n_{2x} & s_x - X \\ n_{1y} & n_{2y} & s_y - Y \\ n_{1z} & n_{2z} & s_z - Z \end{bmatrix}^{-1} \begin{bmatrix} s_x - d_x \\ s_y - d_y \\ s_z - d_z \end{bmatrix}. \quad (2)$$

Equation (2) is applied by the projection processor 40 to each three-dimensional corner point P (in the case of a corner detector) of the three-dimensional set of features 38 using the selected projection geometry 42 to generate corresponding points p of a two-dimensional set of projected features 44.

A registration processor 46 registers the two-dimensional set of projected features 44 with the two-dimensional set of features 36 extracted from the two-dimensional image 30. If the registration entails adjusting projection parameters, then this registration process is optionally iterative, following an iteration loop 48 to re-project the three-dimensional set of features 38 using projection parameters adjusted by the registration in an iterative manner. The output of the registration processor 46 is a set of one or more registration parameters 50. The registration may entail adjustment of various parameters such as projection parameters (e.g., angulation, magnification, source/detector locational parameters, a parameter quantifying pincushion distortion, or so forth), rigid translations or rotations, nonrigid translations or rotations, and so forth. The registration may entail selecting or refining projection parameters of the projection geometry used for the mathematical projecting operation. However, computing the registration parameters 50 based on the complete images 30, 32 is computationally intensive, especially for iterative registration techniques.

The registration parameters 50 are efficiently adjusted by the adjustment processor 46 (optionally including iterative re-projection via loop 48 and projection processor 40) respective to the smaller sets of features 36, 38. As one example, the two-dimensional set of features 36 extracted from the two-dimensional image 30 are taken as the reference, and projection parameters of the projection geometry 42 and/or spatial parameters of the two-dimensional set of projected features 44 are adjusted.

If the projection geometry 42 is accurately or precisely known, for example based on calibrations of the two-dimensional imager 10, and only rigid registration is to be performed, then the optimization space includes only six parameters, e.g. three rotations and three translations respective to the spatial parameters of the two-dimensional set of projected features, and the registration processor 46 can employ a downhill simplex method for numerical adjustment and optimization of these six parameters. The adjustment or optimization is suitably respective to a similarity measure computed (for example) as a sum of the distance squared between each corner point in the two-dimensional set of features 36 and the corresponding projected corner point in the two-dimensional set of projected features 44.

If the projection geometry 42 is not known with sufficient accuracy or precision, then the registration processor 46 optionally adjusts projection parameters of the projection geometry 42 as part of the registration. For example, the projection processor 40 is applied to the three-dimensional set of features 38 with a plurality of different projection angulations deviating by selected amounts from the nominal angulation used in acquiring the two-dimensional image 30. The registration is applied to the two-dimensional set of projected features 44 generated by the mathematical projection at each selected angulation, the "best fit" registration is selected, and the angulation corresponding to the best fit is selected as the adjusted angulation of the adjusted projection geometry 42. This brute force approach is feasible because the dimensionality reduction provided by registering only the features (e.g., corner points) rather than registering entire images provides fast processing. Additionally or alternatively, the angulation or other projection parameters can be included as parameters that are optimized by the registration processor 46 using a least squares minimization or another optimization technique. Optional iterative or exhaustive registration in which the registration processor 46 is applied to different two-dimensional sets of projected features 44 generated by the projection processor 40 with different mathematical projection angulations (or with other variations in the projection geometry 42) are diagrammatically indicated in FIG. 1 by an iteration loop arrow 48.

In most situations, it is anticipated that the projection geometry of the two-dimensional image 30 will be known with a relatively high degree of accuracy, for example based on a calibrated projection geometry of the two-dimensional imager 10 used in acquiring the two-dimensional image 30. In such embodiments, it is generally suitable to assume that each feature in the two-dimensional set of features 36 and the closest feature in the two-dimensional set of projected features 44 both correspond to the same corner point of the subject. In such a case, the similarity measure optimized by the registration processor 46 is suitably computed as a sum of distances-squared where each distance is between a feature of the set of two-dimensional features 36 and the closest feature of the set of two-dimensional projected features 44.

It is contemplated, however, that in some situations, the projection geometry of the two-dimensional image 30 will be known with sufficiently limited precision and/or accuracy that it is not reasonable to assume that each feature in the two-dimensional set of features 36 and the closest feature in the two-dimensional set of projected features 44 both correspond to the same corner point of the subject. In such cases, it is contemplated for the registration processor 46 to apply a combinatoric algorithm to associate features of the two-dimensional set of projected features 44 with corresponding features of the two-dimensional set of features 36 extracted from the two-dimensional image 30.

As further shown in FIG. 1, the adjusted registration parameters 50 are used by an image projector and adjuster 52 to register the respective 2D and 3D images 30, 32 in a second registration step. The registration parameters 50 are adjusted respective to the two-dimensional set of features 36 and the two-dimensional set of projected features 44; however, these features 36, 44 are representative of the spatial characteristics of the respective two- and three-dimensional images 30, 32 and accordingly the registration parameters 50 are applicable in the second registration process performed by the image projector and adjuster 52, which projects the three-dimensional image 32 and adjusts the projected image in accordance with the projection geometry 42 and the registration parameters 50 to produce a two-dimensional projected and registered image 54, which is registered with the two-dimensional image 30.

The projection performed by the image projector and adjuster 52 can employ substantially any type of 3D-to-2D projection method, such as a digitally reconstructed radiograph (DRR) method that sets each point in the projection plane to the line integral mathematically calculated along the line connecting the (virtual) source with the (virtual) point in the projection plane. Other projection methods are also contemplated, such as a maximum intensity projection (MIP) that sets each point in the projection plane to the largest value along the line connecting the (virtual) source with the (virtual) point in the projection plane.

The two-dimensional projected image 54 is suitably compared or combined with the two-dimensional image 30 acquired by the two-dimensional imager 10 by an image processor 56, such as an image combiner or fusion processor, an image comparator, an image display (such as a user interface with a graphical display) and so forth. For example, the 2D image 30 and the 2D projected and registered image 54 can be fused by an image fusion technique and the fused image displayed, or the two images 30, 54 can be displayed side-by-side or in a vertical arrangement. In the latter case, it is contemplated to have locked pointers of a mouse or other pointing device that are displayed at the same spatial position in both of the two displayed images 30, 54 so that a radiologist can readily locate corresponding features in the two images 30, 54.

Although the described registration process is expected to provide accurate and precise results in many cases, in some instances the resulting image registration may be less than fully satisfactory. In some situations, the registered two-dimensional images 30, 54 are compared and, if not aligned within a preselected threshold or to the satisfaction of the radiologist, then subjected to another image registration procedure such as an intensity-based image registration procedure performed by the image processor 56 or another component.

One contemplated application for the multimodality imaging system of FIG. 1 is in the area of interventional cardiac electrophysiology. Interventional cardiac electrophysiology procedures are typically performed under x-ray fluoroscopy for visualizing catheters or other interventional devices relative to highly attenuating structures of the patient such as the thoracic spine and ribs. These projections do not however contain information about soft-tissue anatomy. Accordingly, it is advantageous to fuse these two-dimensional x-ray fluoroscopy images with pre-operatively acquired volumetric cardiac helical or multi-slice CT or MRI images. The system of FIG. 1 provides rapid fusion of the two-dimensional x-ray fluoroscopy images (corresponding to the two-dimensional images 30) with three-dimensional CT or MRI images (corresponding to the three-dimensional images 32) by the image comparator or combiner 56 (which in this embodiment is an image fusion processor) so as to provide real-time visualization of the catheters present within the thorax in relation to the cardiovascular anatomy visible in the volumetric dataset 32.

With reference to FIG. 2, in another contemplated application both imagers of the multimodality imaging system are capable of, and used to, generate three-dimensional images. In other words, in the embodiment of FIG. 2 the two-dimensional imager 10 is replaced by a second three-dimensional imager 60, which may be of the same modality or a different modality as compared with the three-dimensional imager 12. The projection processor 40 is applied to the three-dimensional image generated by the second three-dimensional imager 60 to produce the two-dimensional image 30 having the projection geometry 42, which in this embodiment is a selected geometry used for the mathematical projection of the three-dimensional image generated by the second three-dimensional imager 60. From that point on, the components and processing of the multimodality imaging system of FIG. 2 is analogous to that of the multimodality imager of FIG. 1. The approach of FIG. 2 can provide rapid registration of digitally reconstructed radiographs (DRRs) or other projections generated by different three-dimensional imagers, for example by CT and MRI imagers or by two different CT imagers. Faster processing is possible because the registration is performed in 2D, and moreover is performed only respective to the small features datasets 36, 44.

Those skilled in the art will readily appreciate that the image registration processes disclosed herein can be embodied by a digital storage medium or media storing instructions executable by a digital system to perform the disclosed method. For example, the digital storage medium or media can a magnetic disk, optical disk, magnetic tape, FLASH memory or other electrostatic memory, random access memory (RAM), read-only memory (ROM), Internet server, or so forth, or a combination of such media, and the stored instructions can be executable on a digital system such as a computer, digital network, Internet server, or so forth.

The preferred embodiments have been described. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An image registration process comprising:
    acquiring a two-dimensional image using a two-dimensional imager comprising an x-ray fluoroscopy apparatus;
    acquiring a three-dimensional image using a three-dimensional imager comprising a magnetic resonance imager (MRI) or a computed tomography (CT) imager;
    extracting a two-dimensional set of features from the two-dimensional image;
    extracting a three-dimensional set of features from the three-dimensional image;
    mathematically projecting the three-dimensional set of features into a two-dimensional set of projected features using a projection geometry;
    first registering the two-dimensional set of features and the two-dimensional set of projected features, the first registering including adjusting one or more parameters of the projection geometry selected from a group consisting of an angulation parameter, a magnification parameter, a source location parameter, a detector location parameter, and a distortion parameter; and
    second registering the two-dimensional image and a mathematical projection of the three-dimensional image using parameters derived from the first registering including using the adjusted parameters of the projection geometry for the mathematical projection of the three-dimensional image.

2. The image registration process as set forth in claim 1, wherein the first registering further comprises:
    adjusting spatial parameters of at least one of the two-dimensional set of features and the two-dimensional set of projected features selected from a group consisting of at least three rotation parameters and at least three translation parameters, the adjusted spatial parameters being used in the second registering.

3. The image registration process as set forth in claim 1, wherein the first registering comprises:
optimizing a distance figure-of-merit statistically characterizing distances between features of the two-dimensional set of features and closest corresponding features of the two-dimensional set of projected features.

4. The image registration process as set forth in claim 1, wherein the projection geometry is a projection geometry of a two-dimensional imager during acquisition of the two-dimensional image.

5. The image registration process as set forth in claim 1, wherein the first registering applies a combinatoric algorithm to associate features of the two-dimensional set of features with corresponding features of the two-dimensional set of projected features.

6. The image registration process as set forth in claim 1, further comprising:
displaying a combination, fusion, or comparison of the two-dimensional image and a mathematical projection of the three-dimensional image after the second registering using the parameters derived from the first registering.

7. The image registration process as set forth in claim 1, wherein the extracting operations comprise applying a corner detection algorithm to extract features comprising corner points.

8. The image registration process as set forth in claim 7, wherein the extracting operations further comprise:
applying an edge detection algorithm to extract features comprising line segments.

9. The image registration process as set forth in claim 7, wherein the corner detection algorithm extracts features comprising corner points from the two-dimensional or three-dimensional image by identifying locally maximum eigenvalues of an inertia matrix of the image gradient along a plurality of directions, and identifying a discrete set of line intersections from the identified locally maximum eigenvalues.

10. A non-transitory digital storage medium or media storing instructions executable by a digital system to perform a method comprising:
extracting a two-dimensional set of features from a two-dimensional fluoroscopy image;
extracting a three-dimensional set of features from a three-dimensional magnetic resonance (MR) or computed tomography (CT) image;
mathematically projecting the three-dimensional set of features into a two-dimensional set of projected features using a projection geometry;
first registering the two-dimensional set of features and the two-dimensional set of projected features wherein the first registering includes adjusting projection parameters of the projection geometry; and
second registering the two-dimensional image and a mathematical projection of the three-dimensional image using parameters derived from the first registering;
wherein the extracting operations comprise applying a corner detection algorithm operating on the image gradient to extract features comprising corner points.

11. The non-transitory digital storage medium or media of claim 10, wherein the corner detection algorithm extracts features comprising corner points from the two-dimensional or three-dimensional image by identifying locally maximum eigenvalues of an inertia matrix of the image gradient along a plurality of directions, and identifying a discrete set of line intersections from the identified locally maximum eigenvalues.

12. An image registration apparatus comprising:
an x-ray fluoroscope apparatus configured to acquire a two-dimensional image;
a magnetic resonance imager configured to acquire a three-dimensional image;
a features detector configured to extract a two-dimensional set of features from the two-dimensional image and to extract a three-dimensional set of features from the three-dimensional image;
a projection processor configured to project three-dimensional data into two-dimensional projection data; and
a registration processor configured to
(i) adjust parameters to register the two-dimensional set of features and the three-dimensional set of features projected by the projection processor using a projection geometry, and to
(ii) use the adjusted parameters to register the two-dimensional image and the three-dimensional image projected by the projection processor using the projection geometry,
wherein the registration processor is configured to adjust the projection geometry to register or contribute to registering the two-dimensional set of features and the three-dimensional set of features projected by projection processor.

13. The image registration apparatus as set forth in claim 12, wherein the registration processor is further configured to adjust spatial parameters of at least one of the two-dimensional set of features and the three-dimensional set of features projected by projection processor to register or contribute to registering the two-dimensional set of features and the three-dimensional set of features projected by the projection processor.

14. The image registration apparatus as set forth in claim 12, wherein the features detector comprises a corner detector configured to extract the two-dimensional set of features from the two-dimensional image and to extract the three-dimensional set of features from the three-dimensional image by identifying locally maximum eigenvalues of an inertia matrix of the gradient of the two-dimensional or three-dimensional image along a plurality of directions, and identifying a discrete set of line intersections from the identified locally maximum eigenvalues.

15. The image registration apparatus as set forth in claim 12, wherein the registration processor is configured to adjust the projection geometry including adjusting one or more parameters of the projection geometry selected from a group consisting of an angulation parameter, a magnification parameter, a source location parameter, a detector location parameter, and a distortion parameter to register or contribute to registering the two-dimensional set of features and the three-dimensional set of features projected by projection processor.

16. The image registration apparatus as set forth in claim 12, wherein the features detector comprises a corner detector configured to operate on the image gradient.

17. The image registration apparatus as set forth in claim 16, wherein the features detector further comprises an edge detector.

* * * * *